US00PP28314P3

(12) United States Plant Patent
Brand

(10) Patent No.: US PP28,314 P3
(45) Date of Patent: Aug. 22, 2017

(54) ***SAMBUCUS* PLANT NAMED 'SANIVALK'**

(50) Latin Name: *Sambucus nigra*
Varietal Denomination: SANIVALK

(71) Applicant: Peter Brand, Hatfield (GB)

(72) Inventor: Peter Brand, Hatfield (GB)

(73) Assignee: A. Brand and Sons (GB)

( * ) Notice: Subject to any disclaimer, the term of this patent is extended or adjusted under 35 U.S.C. 154(b) by 159 days.

(21) Appl. No.: 14/756,095

(22) Filed: Jul. 31, 2015

(65) Prior Publication Data

US 2017/0034975 P1 Feb. 2, 2017

(51) Int. Cl.
*A01H 5/00* (2006.01)

(52) U.S. Cl.
USPC ..... Plt./226

(58) Field of Classification Search
USPC ..... Plt./156, 226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Sambucus* cultivar named 'SANIVALK' is disclosed, characterized by a very hardy plant of compact and bushy growth, dark green leaves with narrow cream-colored margins, young leaves with intense yellow margins, and free flowering. The new variety is a *Sambucus* normally produced as an outdoor garden or container plant.

3 Drawing Sheets

Latin name of the genus and species: *Sambucus nigra.*
Variety denomination: 'SANIVALK'.

BACKGROUND OF THE INVENTION

The new cultivar is the product of chance discovery. The new variety originated as a naturally occurring branch mutation of an unpatented unnamed proprietary seedling variety of *Sambucus nigra.*

The new variety was discovered in April of 2013 by the inventor Peter Brand a citizen of England in a nursery in Hatfield, United Kingdom.

Asexual reproduction of the new cultivar was performed by softwood cuttings. This was first performed at a nursery in Hatfield, United Kingdom in Summer of 2013 and has shown that the unique features of this cultivar are stable and reproduced true to type in 3 successive generations.

SUMMARY OF THE INVENTION

The cultivar 'SANIVALK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SANIVALK' These characteristics in combination distinguish 'SANIVALK' as a new and distinct *Sambucus* cultivar:

1. Relatively compact and bushy growth.
2. Mature leaves fresh dark green with narrow cream-colored margins.
3. Young leaves intense yellow margined.
4. Free flowering.
5. Very hardy.

Plants of the new cultivar 'SANIVALK' are similar to plants of the seed parent in most horticultural characteristics, however plants of the new cultivar 'SANIVALK' differs in the following;

1. The new variety has dark green leaves margined with cream whereas the parent has dark green leaves that are not variegated.
2. The new variety has young leaves with intense yellow margin, whereas the parent has no margin coloration.

COMMERCIAL COMPARISON

Plants of the new cultivar 'SANIVALK' are comparable to the unpatented commercial variety *Sambucus* 'Madonna'. The two *Sambucus* varieties are similar in most horticultural characteristics; however, the new variety 'SANIVALK' differs in the following:

1. Mature leaf color of the new variety is dark green narrow cream-colored margins whereas the comparator has dark green leaves broadly margined in cream-colored to yellow-cream.

Plants of the new cultivar 'SANIVALK' can also be comparable to the unpatented commercial variety *Sambucus* 'Marginata'. The two *Sambucus* varieties are similar in most horticultural characteristics; however, the new variety 'SANIVALK' differs in the following:

1. Mature leaf color of the new variety is dark green narrow cream-colored margins whereas the comparator has green leaves with cream-white margins.

BRIEF DESCRIPTION OF THE PHOTOGRAPHS

The accompanying photograph in FIG. 1 illustrates in full color a typical plant of 'SANIVALK' grown outdoors, in a 3 gallon pot. Age of the plant photographed is approximately 1 year old from a rooted cutting.

Figure 1:
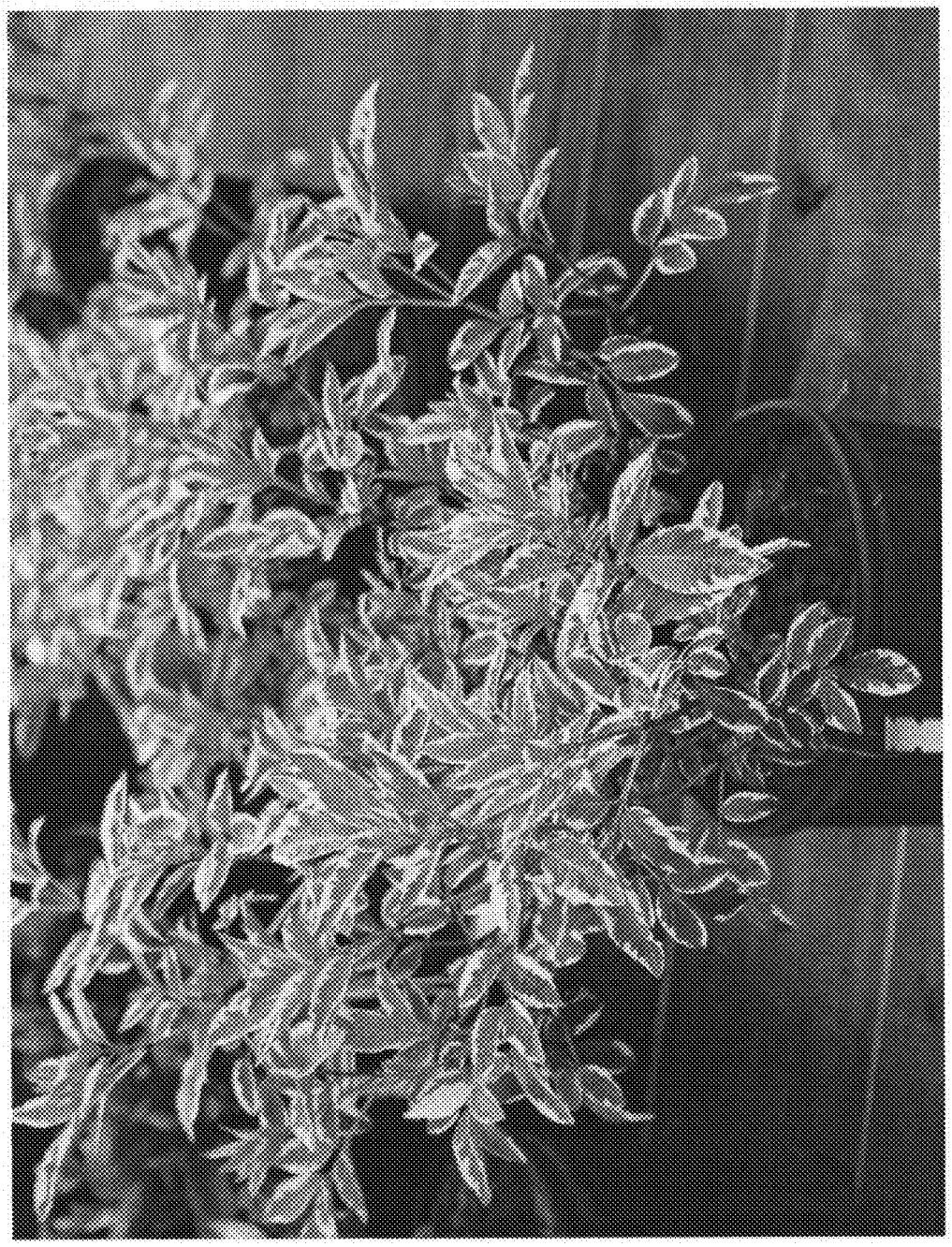
Figure 2:
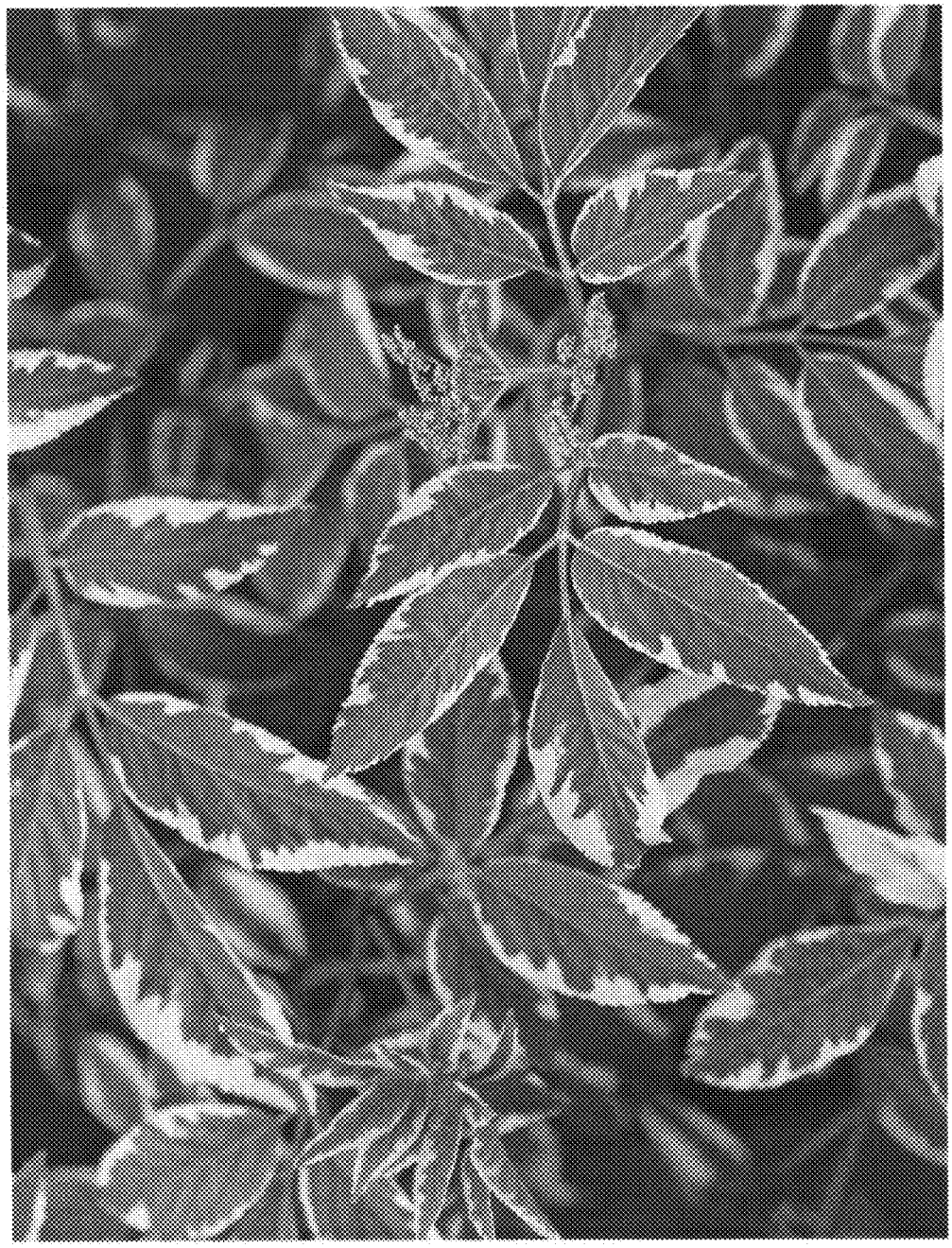
FIG. 2 illustrates a close up of the foliage.
Figure 3:
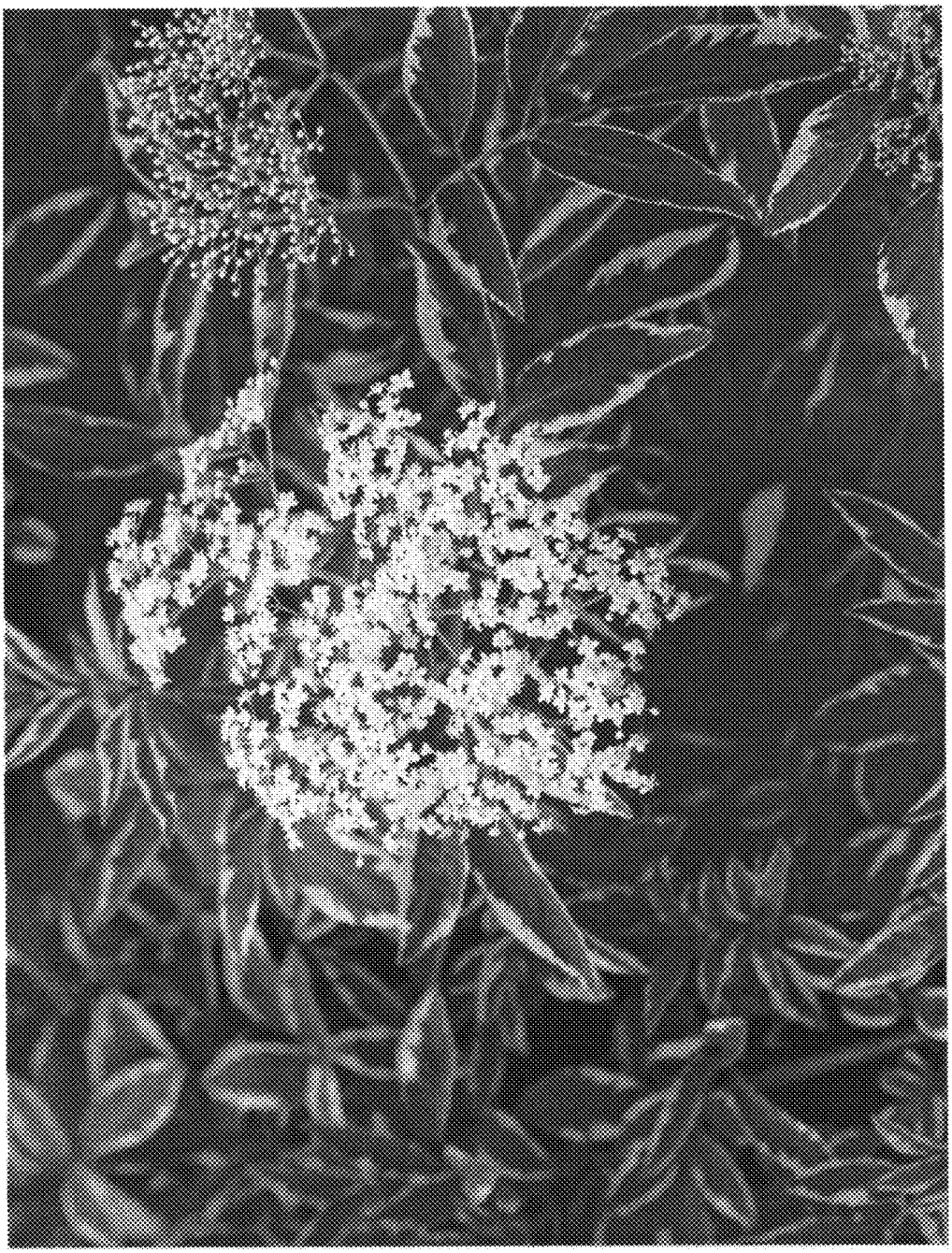
FIG. 3 illustrates flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'SANIVALK' plants grown in March in a poly greenhouse, in Grand Haven, Mich. USA. The growing temperature ranged from 40° F. to 70° F. during the day and from 30° F. to 45° F. during the night. General light conditions are bright, normal sunlight. Measurements and numerical values represent averages of typical plant types. Botanical classification: *Sambucus nigra* 'SANIVALK'.

PROPAGATION

Type of propagation typically used: Softwood cutting.
Time to initiate roots: 21 days at 20° C. average temperature.
Time to produce a rooted young plant: 60 days at 15-20° C. average temperature.
Root description: Moderately dense, moderately free-branching, medium thickness, non-fibrous, fleshy. Color is white.

PLANT

Age of plant described: 1 year from rooted cutting.
Plant type: Perennial shrub.
Container size of the plant described: 3 gallon pot.
Appropriate containers: 1, 2, 3, 5 gallon pots.
Growth habit: Upright, mounded.
Overall plant shape: Upright, mounded.
Height: 0.75 m in a #3 container.
Plant spread: 1 m in a #3 container.
Growth rate: Medium fast.
Crop time to finish: 2¼" pot to #1 in 4 months.
Plant vigor: Good.
Characteristics of primary lateral branches:
- *Quantity.*—8.
- *Branching habit.*—Opposite, Pinching required as shearing helps.
- *Branch appearance.*—Round.
- *Length.*—0.5 m—3 gallon container.
- *Diameter.*—0.7 cm.
- *Color.*—RHS Yellow-green 145A.
- *Pubescence.*—None.
- *Stem aspect/angle.*—20-45°.
- *Strength.*—Good.
- *Other branch characteristics.*—Purpling at nodes RHS Red-purple 60A.

Internode length: Average 11 cm.

FOLIAGE

Leaf:
- *Arrangement.*—Odd-pinnate, compound.
- *Quantity of leaflets per leaf.*—5.
- *Average length.*—6.5-10 cm.
- *Average width.*—3-4.5 cm.
- *Shape.*—Lanceolate.
- *Apex.*—Acute.
- *Base.*—Cuneate.
- *Margin.*—Serrulate.
- *Texture of top surface.*—Smooth.
- *Texture of bottom surface.*—Puberulent.
- *Pubescence.*—Leaf underside.
- *Color.*—Young foliage upper side: Base color RHS Green 143A, variegation Yellow 8A. Young foliage under side: Base color RHS Green 138B, variegation Yellow 3C. Mature foliage upper side: Central color RHS Green 137A. Variegation on margins RHS Yellow-orange 14D, Fade to Green 138B. Mature foliage under side: Central color RHS Green 136B. Variegation on margins RHS Yellow 12D, Fade to Green 138B.
- *Venation.*—Type: Pinnate-netted. Venation color upper side: RHS Green 137A. Venation color under side: RHS Green 136B.
- *Petiole.*—Length: 3 cm. Diameter: 2 mm. Color: Upper side: RHS Green 136B. Lower side: RHS Green 136B. Texture: Upper side: Canaliculated (sunken central groove). Lower side: Smooth.
- *Other traits.*—Variegated margin approx. 0.5 cm from edge.

FLOWER

Flower arrangement: Terminal umbel-like cymes.
Flower shape: Rotate.
Natural flowering season: End April/early May.
Inflorescence height: 10 cm.
Inflorescence width: 16 cm.
Inflorescence and flower type and habit: Umbel of rotate flowers.
Flower longevity on plant: 1-2 weeks.
Persistent or self-cleaning: Self-cleaning.
Quantity of flowers per inflorescence: 220.
Quantity of flowers per plant: 600-700 on a 3 gallon container.
Bud:
- *Shape.*—Spherical.
- *Length.*—3 mm.
- *Diameter.*—2 mm.
- *Color.*—RHS Yellow 11C.

Flower size:
- *Diameter.*—6 mm.
- *Length.*—4 mm.
- *Depth (height).*—4 mm.

Petals:
- *Appearance.*—Rounded facing out.
- *Arrangement.*—Single whorl, not fused.
- *Petal length.*—3 mm.
- *Petal width.*—2 mm.
- *Quantity.*—5.
- *Texture.*—Smooth.
- *Apex.*—Acute.
- *Shape.*—Obovate.
- *Base.*—Obtuse.
- *Margin.*—Entire, slightly undulate.
- *Aspect.*—Upright.

Petal color:
- *When opening.*—Upper surface: RHS White 155D. Lower surface: RHS White 155D.
- *Fully opened.*—Upper surface: RHS White 155D. Lower surface: RHS White 155D.
- *Fading to color.*—Upper and lower: RHS White 155A.

Sepals:
*Quantity per flower.*—4.
*Arrangement.*—Single flat whorl.
*Shape.*—Ovate.
*Length.*—Less than 1 mm.
*Width.*—Less than 1 mm.
*Apex.*—Acute.
*Base.*—Obutuse.
*Margin.*—Entire.
*Texture.*—Upper: Smooth. Lower: Smooth.
*Color.*—Upper Surface: RHS Green 142B. Lower Surface: RHS Green 142B.

Calyx:
*Shape.*—Radial.
*Length.*—1 mm.
*Diameter.*—1 mm.

Peduncle:
*Length.*—8-10 cm.
*Diameter.*—3 mm.
*Angle.*—45°.
*Strength.*—Fibrous softwood, very strong.
*Texture.*—Smooth.
*Color.*—RHS Yellow-green 145B.

Pedicel:
*Length.*—4-6 mm.
*Diameter.*—0.5 mm.
*Color.*—RHS Yellow-green 145B.
*Angle.*—45°.
*Texture.*—Smooth.
*Strength.*—Fibrous, strong.

Fragrance: Very slight/herbaceous.

REPRODUCTIVE ORGANS

Stamens:
*Number.*—4.
*Filament length.*—1 mm.
*Filament color.*—RHS White 155D.

Anthers:
*Shape.*—Oblong.
*Length.*—Less than 1 mm.
*Color.*—RHS yellow 8A.
*Pollen.*—Color: RHS White 155D. Quantity: Lots.

Pistil:
*Number.*—1.
*Length.*—0.5 mm.
*Style.*—Length: less than 1 mm. Color: RHS White 155D.
*Stigma.*—Shape: Truncate. Color: RHS White 155D. Ovary Color: RHS White 155D.

OTHER CHARACTERISTICS

Seeds and fruits: Not observed to date.
Disease/pest resistance: Highly tolerant to pests and diseases.
Lowest temperature tolerance: At least to USDA zone 4.
Highest temperature tolerance: At least to USDA zone 9.
Garden performance: Excellent garden performance; very tolerant to rain and wind.

What is claimed is:

1. A new and distinct cultivar of *Sambucus* plant named 'SANIVALK' as herein illustrated and described.

* * * * *